(12) United States Patent
Zhao

(10) Patent No.: US 10,376,409 B2
(45) Date of Patent: Aug. 13, 2019

(54) TEETH SEPARATING SYSTEM

(71) Applicant: Sherry Zhao, Tampa, FL (US)

(72) Inventor: Sherry Zhao, Tampa, FL (US)

(*) Notice: Subject to any disclaimer, the term of this patent is extended or adjusted under 35 U.S.C. 154(b) by 503 days.

(21) Appl. No.: 14/935,800

(22) Filed: Nov. 9, 2015

(65) Prior Publication Data
US 2016/0045361 A1 Feb. 18, 2016

Related U.S. Application Data

(63) Continuation-in-part of application No. 14/456,662, filed on Aug. 11, 2014, which is a continuation-in-part of application No. 13/200,469, filed on Sep. 23, 2011, now Pat. No. 8,800,568, which is a continuation-in-part of application No. 13/930,905, filed on Jan. 19, 2011.

(51) Int. Cl.
A61F 5/56 (2006.01)

(52) U.S. Cl.
CPC ........ A61F 5/566 (2013.01); A61F 2005/563 (2013.01)

(58) Field of Classification Search
CPC .. A61F 5/566; A61F 2005/563; A63B 71/085; A63B 71/081
USPC ................. 128/861, 859, 857, 846; 433/6, 2
See application file for complete search history.

(56) References Cited

U.S. PATENT DOCUMENTS

| 5,873,365 | A | * | 2/1999 | Brown | A61F 5/56 128/859 |
| 6,932,087 | B1 | * | 8/2005 | Burns | A63B 71/085 128/859 |
| 7,832,404 | B2 | * | 11/2010 | Jansheski | A61F 5/566 128/859 |
| 8,439,044 | B2 | * | 5/2013 | Brown | A61F 5/566 128/846 |
| 2006/0219250 | A1 | * | 10/2006 | Farrell | A63B 71/085 128/859 |
| 2008/0138766 | A1 | * | 6/2008 | Jansheski | A61C 7/08 433/140 |

* cited by examiner

Primary Examiner — Tarla Patel

(57) ABSTRACT

Left and right base components each have upper and lower surfaces in a generally horizontal orientation, an exterior edge, a forward point, a rearward point, and an interior edge. Each base component has a generally oval central extent, a forward extent, and a semicircular rearward extent. A support component in an arcuate configuration is positionable in a generally vertical orientation. The support component has inner and outer faces and upper and lower edges. The upper edge is perpendicular to and integrally formed with the base components at the exterior edge. The support component has terminal ends located adjacent to the base components. The support component has an arcuate forward section between the base components. The lower surface of the base components is spaced from the upper surface of the forward section by an elevational space.

4 Claims, 4 Drawing Sheets

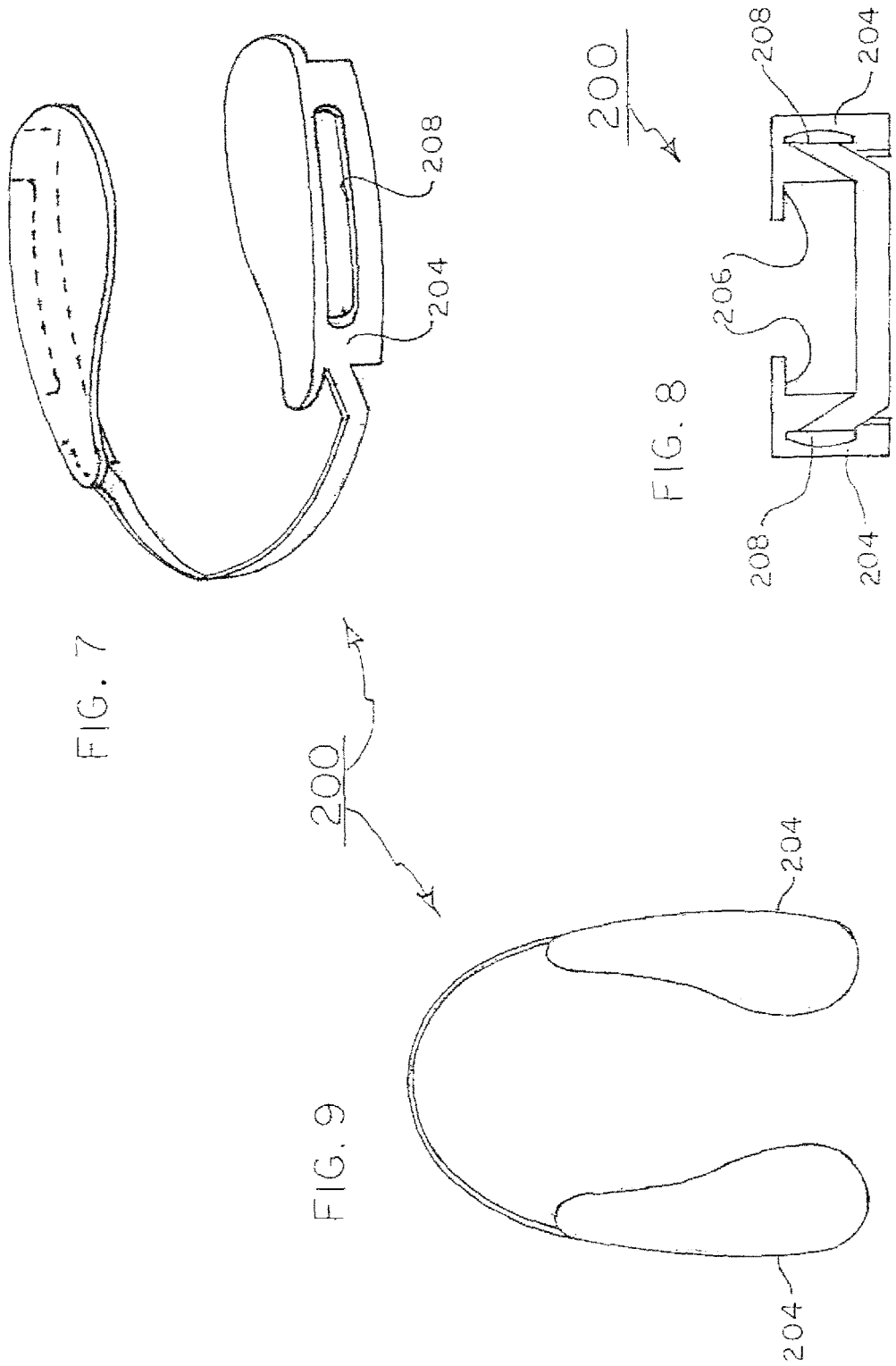

TEETH SEPARATING SYSTEM

The present application is a continuation-in-part of application Ser. No. 14/456,662 filed Aug. 11, 2014, which is a continuation-in-part of pending application Ser. No. 13/200,469 filed Sep. 23, 2011, which is a continuation-in-part of application Ser. No. 12/930,905 filed Jan. 19, 2011, the subject matter of which applications is incorporated herein by reference.

BACKGROUND OF THE INVENTION

Field of the Invention

The present invention relates to a teeth separating system and more particularly pertains to abating teeth grinding through positioning between upper and lower teeth of a user, the abating being done in a safe, convenient, and economical manner.

Description of the Prior Art

The use of teeth separating systems of known designs and configurations is known in the prior art. More specifically, teeth separating systems of known designs and configurations previously devised and utilized for the purpose of abating grinding of teeth are known to consist basically of familiar, expected, and obvious structural configurations, notwithstanding the myriad of designs encompassed by the crowded prior art which has been developed for the fulfillment of countless objectives and requirements.

While these devices fulfill their respective, particular objectives and requirements, they do not describe a teeth separating system that allows abating teeth grinding through positioning between upper and lower teeth of a user, the abating being done in a safe, convenient, and economical manner.

In this respect, the teeth separating system according to the present invention substantially departs from the conventional concepts and designs of the prior art, and in doing so provides an apparatus primarily developed for the purpose of abating teeth grinding through positioning between upper and lower teeth of a user, the abating being done in a safe, convenient, and economical manner.

Therefore, it can be appreciated that there exists a continuing need for a new and improved teeth separating system which can be used for abating teeth grinding through positioning between upper and lower teeth of a user, the abating being done in a safe, convenient, and economical manner. In this regard, the present invention substantially fulfills this need.

SUMMARY OF THE INVENTION

In view of the foregoing disadvantages inherent in the known types of teeth separating systems of known designs and configurations now present in the prior art, the present invention provides an improved teeth separating system. As such, the general purpose of the present invention, which will be described subsequently in greater detail, is to provide a new and improved teeth separating system and method which has all the advantages of the prior art and none of the disadvantages.

To attain this, the present invention essentially comprises a teeth separating system comprising a left base component and a right base component. Each base component has upper and lower surfaces in a generally horizontal orientation. Each base component has an exterior edge, a forward point, a rearward point, and an interior edge. Each base component has a generally oval central extent and a forward extent and a semicircular rearward extent. A support component in an arcuate configuration is positional in a generally vertical orientation. The support component has inner and outer faces. The support component has upper and lower edges. The upper edge is perpendicular to and integrally formed with the base components at the exterior edge. The support component has terminal ends located adjacent to the base components. The support component has an arcuate forward section between the base components. The lower surface of the base components is spaced from the upper surface of the forward section by an elevational space.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved teeth separating system which has all of the advantages of the prior art teeth separating systems of known designs and configurations and none of the disadvantages.

It is another object of the present invention to provide a new and improved teeth separating system which may be easily and efficiently manufactured and marketed.

It is further object of the present invention to provide a new and improved teeth separating system which is of durable and reliable constructions.

An even further object of the present invention is to provide a new and improved teeth separating system which is susceptible of a low cost of manufacture with regard to both materials and labor, and which accordingly is then susceptible of low prices of sale to the consuming public, thereby making such teeth separating system economically available to the buying public.

Lastly, even still another object of the present invention is to provide a teeth separating system for abating teeth grinding through positioning between upper and lower teeth of a user, the abating being done in a safe, convenient, and economical manner.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 7 is a perspective illustration of a teeth separating system constructed in accordance with the principles of the present invention.

FIG. 8 is a front elevational view of the system shown in FIG. 7.

FIG. 9 is a plan view of the system shown in FIGS. 7 and 8.

The same reference numerals refer to the same parts throughout the various Figures.

DESCRIPTION OF THE PREFERRED EMBODIMENT

Figure 1:
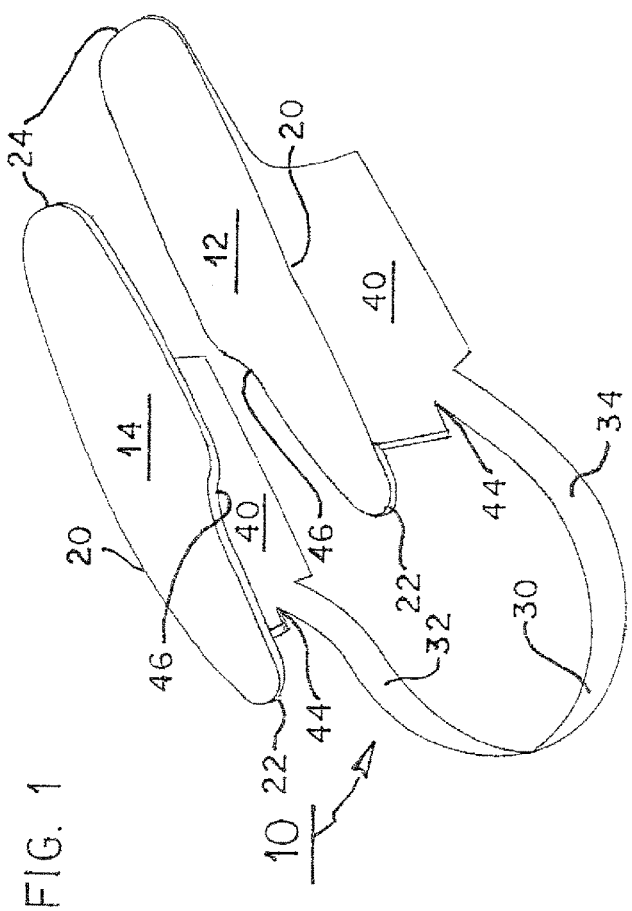
FIG. 1 is a perspective illustration of a teeth separating system constructed in accordance with the principles of the present invention.
Figure 2:
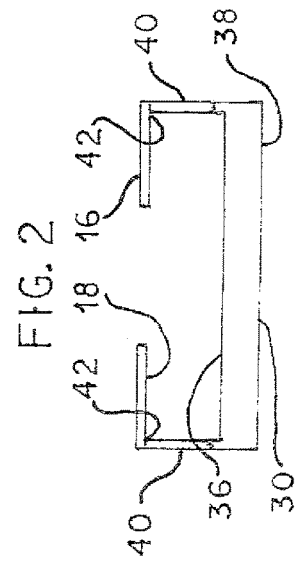
FIG. 2 is a front elevational view of the system shown in FIG. 1.
Figure 3:
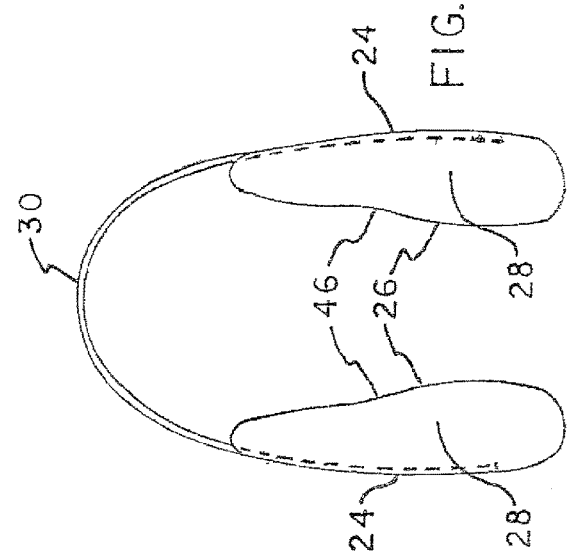
FIG. 3 is a plan view of the system shown in FIGS. 1 and 2.

With reference now to the drawings, and in particular to FIG. 1 thereof, the preferred embodiment of the new and improved teeth separating system embodying the principles and concepts of the present invention and generally designated by the reference numeral 10 will be described.

The present invention, the teeth separating system 10 is comprised of a plurality of components. Such components in their broadest context include a left base component, a right base component, and a support component. Such components are individually configured and correlated with respect to each other so as to attain the desired objective.

The teeth separating system 10 is for abating tooth grinding through positioning between upper and lower teeth of a user. The abating is done in a safe, convenient, and economical manner. First provided is a left base component 12 and a similarly configured right base component 14. The left base component and the right base component are positionable in a generally horizontal plane when in use between the teeth of a user while the user is in an upright position, i.e., standing or sitting. Each base component has an upper surface 16 positional in contact with the upper teeth of the user during use and a lower surface 18 positional in contact with the lower teeth of the user during use. The upper and lower surfaces are separated by a thickness of from 1.0 to 4.0 millimeters throughout their entire extents. Each base component has an exterior edge 20 with a central forward point 22 and laterally spaced rearward points 24.

Each base component has an interior edge 26. Each base component has an oval central extent 28 with a length of 33 millimeters plus or minus 10 percent. Each base component has arcuate forward extents with a first width. Each base component has a semicircular rearward extent with a second width which is greater than the first width.

A support component 30 is next provided. The support component is in an arcuate configuration. The support component is positional in a generally vertical orientation when in use exterior of the gums and interior of the cheeks and lower lip of the user while the user is in an upright position, i.e., standing or sitting. The support component has an inner face 32 and an outer face 34. The inner and outer faces are separated by a thickness of from 1.0 millimeters to 4.0 millimeters throughout their entire extent. The support component has an upper edge 36 and a lower edge 38. The upper edge is perpendicular to and integrally formed with the base component at the exterior periphery. The support component has a height of 5 to 10 millimeters with enlarged rearward sections. The support component has terminal ends spaced from the rearward points of the base components. The vertical distance or height between the base components measured from their lower surfaces and the support component measured from it lower edge is from 1 centimeter to 2 centimeters. The width of the enlarged rearward sections measured horizontally is from 1.5 centimeters to 2.5 centimeters.

The enlarged rearward sections 40 are formed in the support component. Each enlarged rearward section is located beneath an associated one of the base components. Two coupling lines 42 are next provided. Each coupling line is located between an associated one of the enlarged regions and an associated one of the base components. Each coupling line extends rearwardly of an associated one of the forward points to forwardly of an associated one of the rearward points. A notch 44 cut-out in each enlarged region is provided intermediate each enlarged region and the support component. The interior edge of each base component is formed with an S-shaped curve 46 above the enlarged rearward sections.

The system is fabricated in one piece of a material with limited flexibility and elasticity. The material is chosen from the class of materials with limited flexibility and elasticity including silicone and thermoplastic elastomer and latex and plastic and organic materials.

Figure 4:
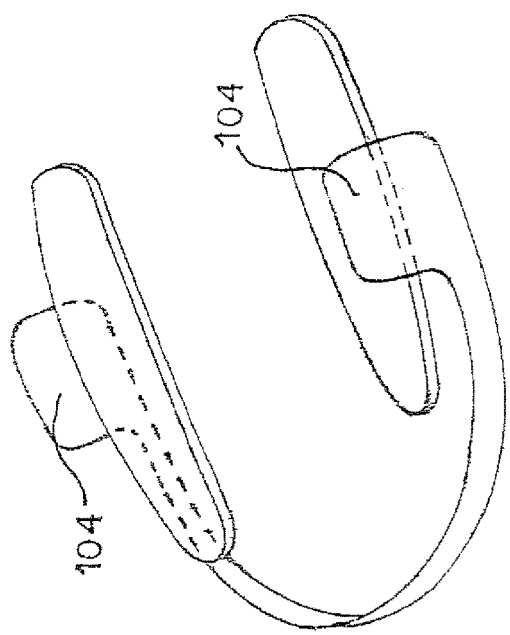
FIG. 4 is a perspective illustration of a teeth separating system constructed in accordance with the principles of the present invention.
Figure 5:
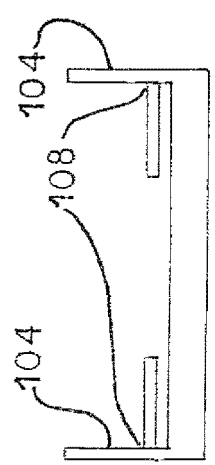
FIG. 5 is a front elevational view of the system shown in FIG. 4.
Figure 6:
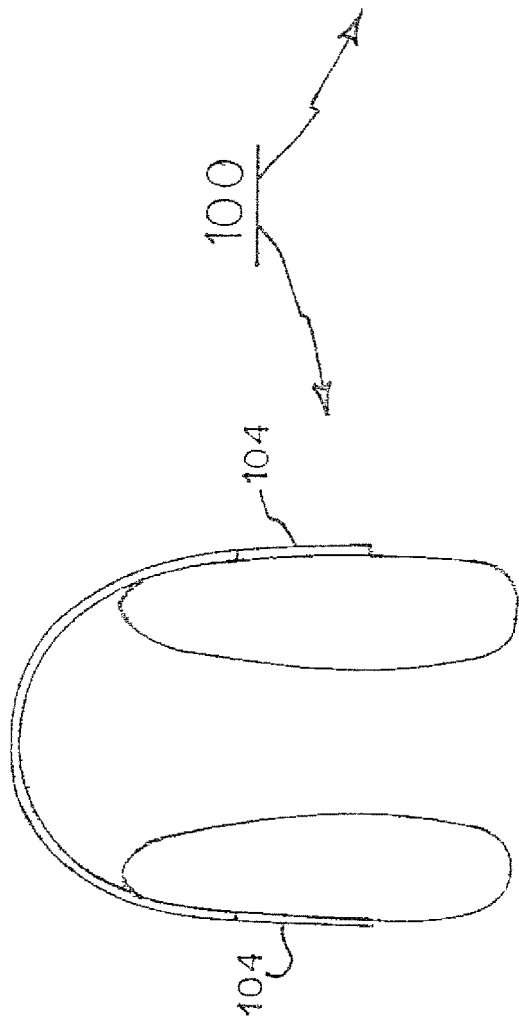
FIG. 6 is a plan view of the system shown in FIGS. 4 and 5.

An alternate embodiment of the invention is shown in FIGS. 4, 5 and 6. In this embodiment, the system 100 further includes two enlarged regions 104 formed in the support component. Each enlarged region 104 has an upper edge and a lower edge. Two coupling lines 108 are provided. Each coupling line is located between an associated enlarged region and associated base component. Each enlarged region has a common height measured vertically, two coupling lines (206), each enlarged region having a height of from 1.0 to 2.0 centimeters, each enlarged region having a width measured horizontally of from 1.5 to 2.5 centimeters, each enlarged region having a thickness of from 1.0 to 4.0 millimeters, each coupling line being located between an associated enlarged region and associated base component, a rectangular cut-out (208) formed in each enlarged region.

Another alternate embodiment of the invention is shown in FIGS. 7, 8 and 9. In the embodiment, the system 200 further includes two enlarged regions 204 formed in the support component. Each enlarged region is located beneath an associated base component. Further provided are two coupling lines 206. Each coupling line is located between an associated enlarged region and associated base component. Each enlarged region has a height measured vertically from 1.0 to 2.0 centimeters. Each enlarged region has a width measured horizontally of from 1.5 to 2.5 centimeters. Each enlarged region has a thickness of from 1.0 to 4.0 millimeters, A rectangular cut-out 208 is formed in each enlarged region. Each rectangular cut out has a height between 25 percent and 75 percent of the height of each enlarged region. Each rectangular cut out has a width between 25 percent and 75 percent of the width of each enlarged region.

The two enlarged regions 204 are formed in the ends of the support component. Each enlarged region is located beneath an associated base component. The upper edge of the support component forms, with the enlarged regions, upper notches at acute angles. The lower edge of the support component forms, with the enlarged regions, lower notches at an acute angle.

The first three embodiments each illustrate the forward most point of each base component located forwardly of the forward most point of its supporting enlarged rearward section. Each embodiment also illustrates the rearward most point of each base component located rearwardly of the rearward most point of its supporting enlarged rearward section. It should be understood, however, that the forward most point of each base component may be located at or adjacent to the forward most point of its supporting enlarged rearward section. Similarly, the rearward most point of each base component may be located at or adjacent to the rearward most point of its supporting enlarged rearward section.

Figure 10:
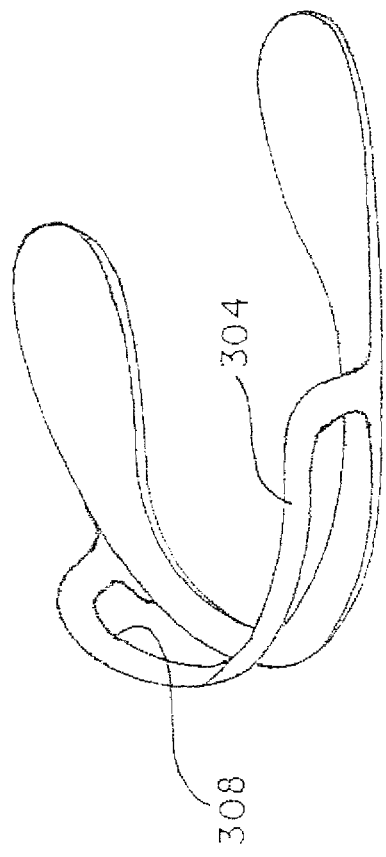
FIG. 10 is a perspective illustration of a teeth separating system constructed in accordance with the principles of the present invention.
Figure 11:
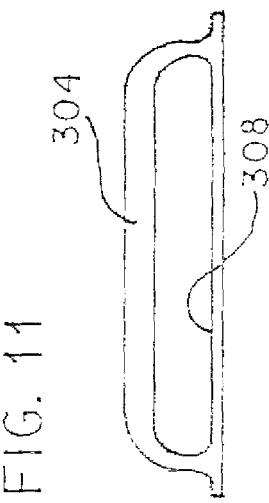
FIG. 11 is a front elevational view of the system shown in FIG. 10.
Figure 12:
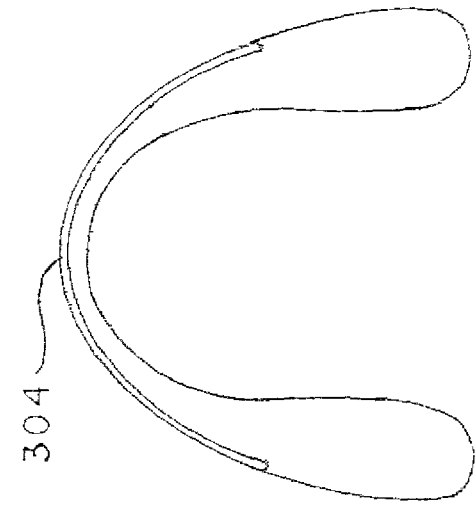
FIG. 12 is a plan view of the system shown in FIGS. 10 and 11.

A final embodiment of the invention is shown in FIGS. 10, 11 and 12. In this embodiment of the system 300, the support component 304 is located totally between the base components. In this embodiment, the system further includes a rectangular cut-out 308 extending through the support component which extends upwardly. Each rectangular cut out has a height between 25 percent and 75 percent of the height of each enlarged region. Each rectangular cut out has a width between 25 percent and 75 percent of the width of each enlarged region.

It should be understood that the support component for any of the disclosed embodiments including FIG. 10 may be a single arcuate element as illustrated in FIGS. 1, 4, and 7. Conversely, it should be understood that the support component for any of the disclosed embodiments including FIGS. 1, 4, and 7 may include two elevationally spaced arcuate elements as illustrated in FIG. 10.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A teeth separating system comprising:
    a left base component and a right base component, each base component having upper and lower surfaces in a generally horizontal orientation, each base component having an exterior edge, a forward point, a rearward point, and an interior edge, each base component having a generally oval central extent and a forward extent and a semicircular rearward extent; and
    a support component in an arcuate configuration positionable in a generally vertical orientation, the support component having inner and outer faces, the support component having upper and lower edges, the upper edge being perpendicular to and integrally formed with the base components at the exterior edge, the support component having terminal ends located adjacent to the base components, the support component having an arcuate forward section between the base components, the lower surfaces of the base components being spaced from the upper surface of the forward section by an elevational space, two enlarged regions (204) formed in the support component, each enlarged region being located beneath an associated base component, each enlarged region having a common height measured vertically, two coupling lines (206), each coupling line being located between an associated enlarged region and associated base component, each enlarged region having a height measured vertically from 1.0 to 2.0 centimeters, each enlarged region having a width measured horizontally of from 1.5 to 2.5 centimeters, each enlarged region having a thickness of from 1.0 to 4.0 millimeters, a rectangular cut-out (208) formed in each enlarged region, each rectangular cut out having a height between 25 percent and 75 percent of the height of each enlarged region, each rectangular cut out having a width between 25 percent and 75 percent of the width of each enlarged region.

2. The system as set forth in claim 1 and further including:
    two enlarged regions formed in the support component, each enlarged region being located beneath an associated base component, two coupling lines, each coupling line being located between an associated enlarged region and an associated base component, each coupling line extending rearwardly of an associated forward point to forwardly of an associated rearward point, a notch cut-out of each enlarged region intermediate each enlarged region and the support component, the interior edge of each base component being formed with an S-shaped curve above the enlarged regions.

3. A teeth separating system comprising:
    a left base component and a right base component, each base component having upper and lower surfaces in a generally horizontal orientation, each base component having an exterior edge, a forward point, a rearward point, and an interior edge, each base component having a generally oval central extent and a forward extent and a semicircular rearward extent; and
    a support component in an arcuate configuration positionable in a generally vertical orientation, the support component having inner and outer faces, the support component having upper and lower edges, the upper edge being perpendicular to and integrally formed with the base components at the exterior edge, the support component having terminal ends located adjacent to the base components, the support component having an arcuate forward section between the base components, the lower surfaces of the base components being spaced from the upper surface of the forward section by an elevational space;

two enlarged regions (204) formed in the support component, each enlarged region being located beneath an associated base component, the upper edge of the support component forming, with the enlarged regions, upper notches at acute angles, the lower edge of the support component forming, with the enlarged regions, lower notches at an acute angle;

two coupling lines (206), each coupling line being located between an associated enlarged region and associated base component, each enlarged region has a height measured vertically from 1.0 to 2.0 centimeters, each enlarged region having a width measured horizontally of from 1.5 to 2.5 centimeters, each enlarged region has a thickness of from 1.0 to 4.0 millimeters;

rectangular cut-out 208 is formed in each enlarged region, each rectangular cut out having a height between 25 percent and 75 percent of the height of each enlarged region, each rectangular cut out having a width between 25 percent and 75 percent of the width of each enlarged region.

4. The system as set forth in claim 1 wherein the support component is a single arcuate element.

* * * * *